US00PP18862P2

(12) United States Plant Patent

Gross et al.

(10) Patent No.: US PP18,862 P2

(45) Date of Patent: Jun. 3, 2008

(54) *IMPATIENS* PLANT NAMED 'BALFUSHIMGLO'

(50) Latin Name: *Impatiens walleriana×Impatiens auricoma*
Varietal Denomination: Balfusimglo

(75) Inventors: Kristen Nicole Gross, DeKalb, IL (US); Tau-San Chou, Batavia, IL (US)

(73) Assignee: Ball Horticultural Company, West Chicago, IL (US)

( * ) Notice: Subject to any disclaimer, the term of this patent is extended or adjusted under 35 U.S.C. 154(b) by 74 days.

(21) Appl. No.: 11/602,757

(22) Filed: Nov. 21, 2006

(51) Int. Cl.
*A01H 5/00* (2006.01)

(52) U.S. Cl. ..... Plt./317

(58) Field of Classification Search ..... Plt./317
See application file for complete search history.

*Primary Examiner*—Annette H Para

(74) *Attorney, Agent, or Firm*—Audrey Charles

(57) ABSTRACT

A new and distinct cultivar of *Impatiens* plant named 'Balfusimglo', characterized by its light yellow-colored flowers, medium green-colored foliage, and moderately vigorous, upright-mounded growth habit.

1 Drawing Sheet

Latin name of genus and species of plant claimed: *Impatiens walleriana×Impatiens auricoma.*
Variety denomination: 'Balfusimglo'.

BACKGROUND OF THE INVENTION

The present invention relates to a new and distinct cultivar of *Impatiens* plant botanically known as *Impatiens walleriana×Impatiens auricoma* and hereinafter referred to by the cultivar name 'Balfusimglo'.

The new cultivar originated in a controlled breeding program in Elburn, Ill. during September 1999. The objective of the breeding program was the development of *Impatiens* hybrid cultivars with numerous flowers, unique flower coloration and flower shape, excellent basal branching, and an upright, compact to moderate growth habit.

The new *Impatiens* cultivar is the result of cross-pollination. The female (seed) parent of the new cultivar is the proprietary *Impatiens walleriana* breeding selection designated 9516-4, not patented, characterized by its medium coral-colored flowers, medium green-colored foliage, and upright growth habit. The male (pollen) parent of the new cultivar is the proprietary *Impatiens auricoma* breeding selection designated 193, not patented, characterized by its medium yellow-colored flowers, medium green-colored foliage, and upright growth habit. The new cultivar was discovered and selected as a single flowering plant within the progeny of the above stated cross-pollination during March 2001 in a controlled environment at Elburn, Ill.

Asexual reproduction of the new cultivar by terminal stem cuttings since March 2001 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balfusimglo' as a new and distinct cultivar of *Impatiens* plant:

1. Light yellow-colored flowers;
2. Medium green-colored foliage; and
3. Moderately vigorous, upright-mounded growth habit.

Plants of the new cultivar differ from plants of the female parent primarily in flower color and flower shape and from plants of the male parent primarily in flower color.

Of the many commercially available *Impatiens* cultivars known to the inventor, the most similar in comparison to the new cultivar is Fusion™ 'Balfusglo', U.S. Plant Pat. No. 15,168. However, in side by side comparisons, plants of the new cultivar differ from plants of 'Balfusglo' in the following characteristics:

1. Plants of the new cultivar have smaller flowers than plants of 'Balfusglo'; and
2. Plants of the new cultivar have smaller leaves than plants of 'Balfusglo'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfusimglo'. The plants were grown in 4.5 inch pots for 10 weeks in a greenhouse at West Chicago, Ill.

DETAILED BOTANICAL DESCRIPTION

Figure 1:
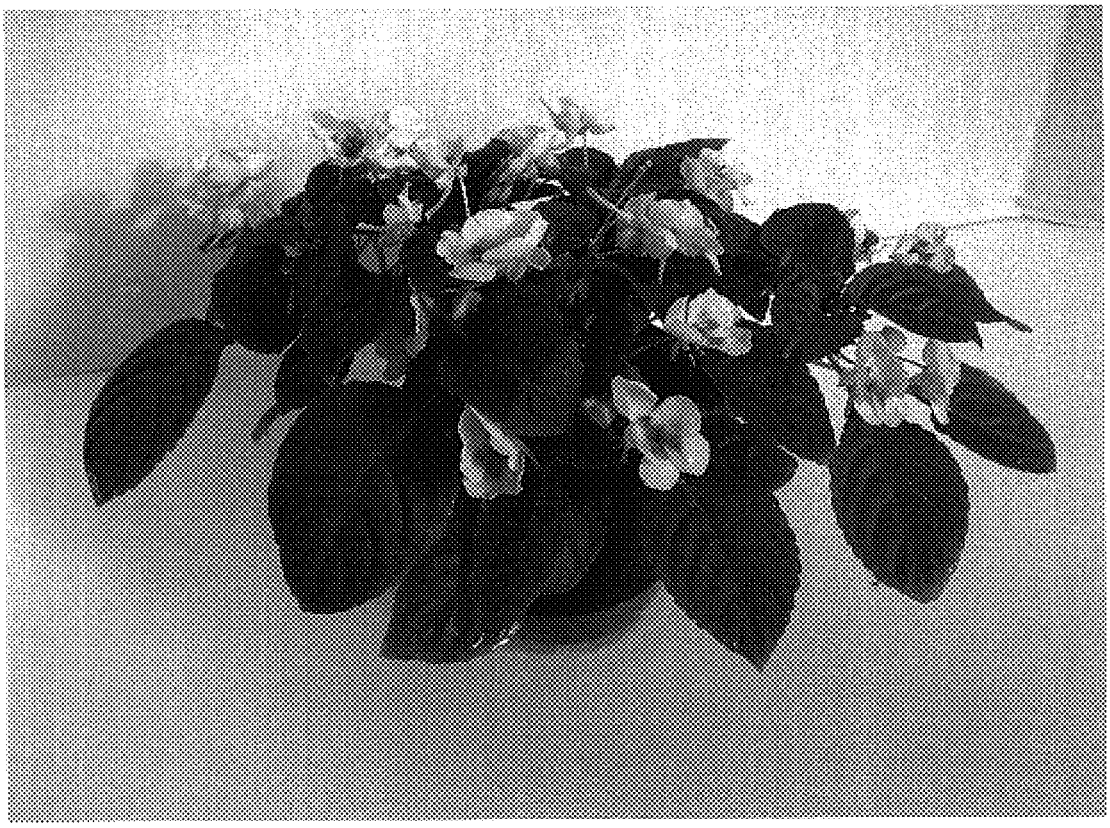
FIG. 1 illustrates a side view of the overall growth and flowering habit of 'Balfusimglo'.
Figure 2:
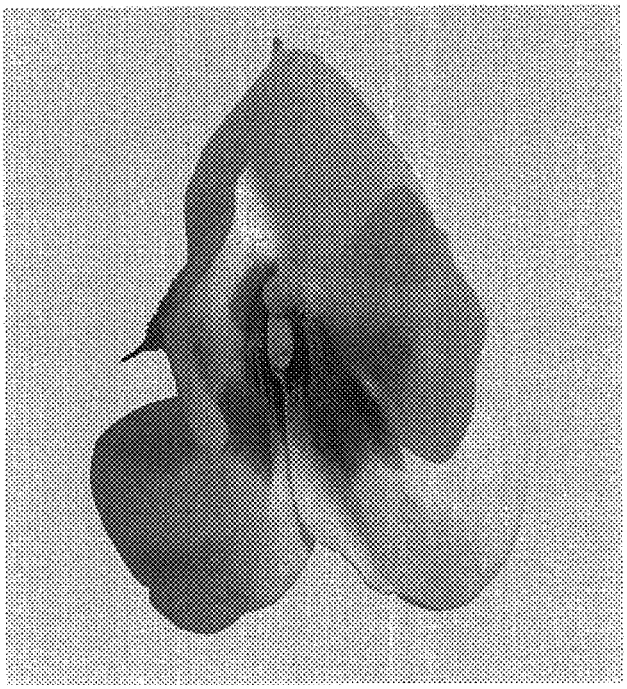
FIG. 2 illustrates a close-up view of an individual flower of 'Balfusimglo'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Feb. 14, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 10 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens wallerianaxImpatiens auricoma* cultivar Balfusimglo.

Parentage:

*Female parent.*—Proprietary *Impatiens walleriana* breeding selection designated 9516-4, not patented.

*Male parent.*—Proprietary *Impatiens auricoma* breeding selection designated 193, not patented.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 6 to 9 weeks from a rooted cutting.

*Growth habit and general appearance.*—Moderately vigorous, upright-mounded.

*Size.*—Height from soil level to top of plant plane: Approximately 11.9 cm. Width: Approximately 35.6 cm.

*Branching habit.*—Freely basal branching. Quantity of main branches per plant: Approximately 5.

*Branch.*—Strength: Moderately strong. Length: Approximately 11.6 cm. Diameter: Approximately 6.1 mm. Length of central internode: Approximately 2.3 cm. Texture: Glabrous. Color of young and mature stems: 146C with streaks of 187B primarily at nodes.

Foliage description:

*General description.*—Quantity of leaves per main branch: Approximately 11. Fragrance: None. Form: Simple. Arrangement: Lower leaves alternate and upper leaves are in whorls.

*Leaves.*—Aspect: Petiole is at an acute angle to stem and leaves are perpendicular to an obtuse angle to stem. Shape: Elliptic. Margin: Crenate with ciliation. Apex: Acuminate. Base: Attenuate. Venation pattern: Pinnate. Length of mature leaf at center of stem: Approximately 7.3 cm. Width of mature leaf at center of stem: Approximately 5.0 cm. Texture of upper and lower surfaces: Glabrous. Color of upper surface of young foliage: 137A with venation of 138C. Color of lower surface of young foliage: Between 138B and 138C with venation of 138C. Color of upper surface of mature foliage: 137A with venation of 138D. Color of lower surface of mature foliage: Between 138B and 138C with venation of 138D.

*Petiole.*—Length: Approximately 3.4 cm. Diameter: Approximately 2.1 mm. Texture: Glabrous. Color: 138D with an overlay of 187D.

Flowering description:

*Flowering habit.*—'Balfusimglo' is freely flowering under outdoor growing conditions with substantially continuous blooming from spring through autumn and year-round in greenhouse environment.

*Lastingness of individual flower on the plant.*—Approximately 3 to 5 days.

Flower description:

*General description.*—Type: Single. Quantity per plant: Approximately 18. Fragrance: None.

*Bud.*—Rate of opening: Generally takes 1 to 2 days for bud to progress from first color to fully open flower. Quantity showing color per plant: Approximately 5.

*Bud just before opening.*—Shape: Ovoid. Length: Approximately 1.2 cm. Diameter: Approximately 1.1 cm. Color: 15D.

*Corolla.*—Shape: Oval, cupped when first open, becoming flatter with age. Length: Approximately 3.6 cm. Width: Approximately 2.7 cm. Depth: Approximately 1.2 cm. Borne: Above and below the foliage.

*Petals.*—Quantity: 5. Shape of upper petal: Cucullate. Shape of lateral and lower petals: Obovate. Aspect: Cupped. Appearance: Iridescent. Margin: Entire. Apex of upper petal: Emarginate. Apex of lateral and lower petals: Obtuse. Base of upper petal: Truncate. Base of lateral and lower petals: Attenuate. Length of upper petal: Approximately 1.5 cm. Width of upper petal: Approximately 1.3 cm. Length of lateral petals: Approximately 1.5 cm. Width of lateral petals: Approximately 1.5 cm. Length of lower petals: Approximately 1.7 cm. Width of lower petals: Approximately 1.5 cm. Texture of upper and lower surfaces: Glabrous. Color of upper surface when first open and fully open: 10C with an eye of 46A. Lateral petals have a faint spot of 32B near the lower edge, and lower petals have a spot of 32B on lower portion. Color of lower surface when first open and fully open: 10C.

*Spur.*—Quantity: 1 per flower, double-tipped. Aspect: Moderately curved downward. Length: Approximately 1.6 cm. Diameter at tip: Approximately 2.0 mm. Diameter at base: Approximately 3.0 mm. Texture: Glabrous. Color: 1C at flower base transitioning to 144D at tip.

*Peduncle.*—Strength: Strong. Aspect: Acute angle to stem. Length: Approximately 2.9 cm. Diameter: Approximately 1.0 cm. Texture: Glabrous. Color: 144B.

*Sepals.*—Quantity per flower: 4, with one fused to base of upper petal. Shape of lateral sepals: Elliptic. Shape of lower sepal: Ovate. Base of lower sepal is modified to form a spur. Apex of all sepals: Acuminate. Length of lateral sepals: Approximately 1.1 cm. Width of lateral sepals: Approximately 5.5 mm. Length of lower sepal: Approximately 1.6 cm. Width of lower sepal: Approximately 1.1 cm. Texture of upper and lower surfaces of all sepals: Glabrous. Color of lateral sepals: 1D transitioning to 144C at apex. Color of lower sepal: 3A with 144C at tip and streaks of 46A at base of upper surface.

*Reproductive organs.*—Androecium: Stamen quantity: 5 per flower, fused around pistil at apex. Anther shape: Oval. Anther length: Approximately 1.0 mm. Anther color: 13C. Pollen amount: None observed. Gynoecium: Pistil quantity: 1 per flower. Pistil length: Approximately 5.6 mm. Stigma shape: 5-pointed star. Stigma color: Colorless, translucent. Style color: Colorless, translucent. Ovary texture: Glabrous. Ovary color: 149A.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balfusimglo', substantially as herein shown and described.

* * * * *

UNITED STATES PATENT AND TRADEMARK OFFICE

CERTIFICATE OF CORRECTION

PATENT NO. : PP 18,862 P2
APPLICATION NO. : 11/602757
DATED : June 3, 2008
INVENTOR(S) : Kristen Nicole Gross and Tau-San Chou It is certified that error appears in the above-identified patent and that said Letters Patent is hereby corrected as shown below:

on the title page, item (54)

change “Balfushimglo” to --Balfusimglo--

Signed and Sealed this

Twenty-ninth Day of July, 2008

JON W. DUDAS
*Director of the United States Patent and Trademark Office*